United States Patent [19]

Cioca et al.

[11] Patent Number: 4,999,348

[45] Date of Patent: Mar. 12, 1991

[54] LIQUID CRYSTAL CONTAINING COSMETIC AND PHARMACEUTICAL COMPOSITIONS AND METHODS FOR UTILIZING SUCH COMPOSITIONS

[75] Inventors: Gheorghe Cioca, Lake Grove; James A. Hayward, Port Jefferson; Manuel L. Tan, Glen Cove; Morris Herstein, Scarsdale, all of N.Y.; Walter P. Smith, Stamford, Conn.

[73] Assignee: Estee Lauder Inc., New York, N.Y.

[21] Appl. No.: 131,458

[22] Filed: Dec. 11, 1987

[51] Int. Cl.⁵ ............................................ A61K 31/56
[52] U.S. Cl. .................................... 514/171; 514/182
[58] Field of Search ............... 514/170, 171, 180, 182

[56] References Cited

U.S. PATENT DOCUMENTS

| | | | |
|---|---|---|---|
| 3,409,404 | 11/1968 | Fergason | 23/230 |
| 3,441,513 | 4/1969 | Woodmansee | 252/408 |
| 3,445,563 | 5/1969 | Clegg | 424/35 |
| 3,529,156 | 9/1970 | Fergason et al. | 250/83 |
| 3,533,399 | 10/1970 | Goldberg | 128/2 |
| 3,576,761 | 4/1971 | Davis | 252/408 |
| 3,600,060 | 8/1971 | Churchill | 350/160 |
| 3,619,254 | 11/1971 | Davis | 117/72 |
| 3,766,061 | 10/1973 | Mahler | 252/1 |
| 3,771,065 | 11/1973 | Goldberg et al. | 331/94.5 L |
| 3,885,982 | 5/1975 | Fergason | 106/252 |
| 3,906,108 | 9/1975 | Felty | 424/318 |
| 3,920,574 | 11/1975 | Brown, Jr. et al. | 252/299 |
| 3,969,264 | 7/1976 | Davis | 252/299 |
| 3,974,317 | 8/1976 | Sharpless | 428/215 |
| 3,991,184 | 11/1976 | Kludas et al. | 424/177 |
| 3,998,860 | 12/1976 | Brown, Jr. et al. | 260/397.2 |
| 4,022,706 | 5/1977 | Davis | 252/299 |
| 4,045,383 | 8/1977 | Koff | 260/8 |
| 4,150,114 | 4/1979 | Smith | 424/60 |
| 4,151,304 | 4/1979 | Evans | 424/361 |
| 4,170,229 | 10/1979 | Olson | 128/67 |
| 4,301,023 | 11/1981 | Schuberth et al. | 252/299.7 |
| 4,301,054 | 11/1981 | Buirley et al. | 260/29.4 |
| 4,309,448 | 1/1982 | Takaishi et al. | 424/365 |
| 4,348,415 | 9/1982 | Tsutsumi et al. | 424/365 |
| 4,354,385 | 10/1982 | Fraschini | 374/162 |
| 4,375,480 | 3/1983 | Soma | 424/358 |
| 4,393,044 | 7/1983 | Takada et al. | 424/59 |
| 4,441,508 | 4/1984 | Buirley et al. | 128/736 |
| 4,501,503 | 2/1985 | Buirley et al. | 374/162 |
| 4,524,778 | 6/1985 | Brown, Jr. et al. | 128/736 |
| 4,524,779 | 6/1985 | Brown, Jr. | 128/736 |
| 4,525,344 | 6/1985 | Tutsky | 424/73 |
| 4,600,526 | 7/1986 | Gallot et al. | 252/299.01 |
| 4,603,146 | 7/1986 | Kligman | 514/559 |
| 4,656,031 | 4/1987 | Lane et al. | 424/49 |
| 4,673,567 | 6/1987 | Jizomoto | 424/38 |
| 4,690,825 | 9/1987 | Won | 424/501 |
| 4,691,712 | 9/1987 | Brown, Jr. | 125/736 |
| 4,702,913 | 10/1987 | Marty | 424/95 |
| 4,703,041 | 10/1987 | Weber et al. | 514/23 |

FOREIGN PATENT DOCUMENTS

| | | |
|---|---|---|
| 1108838 | 9/1981 | Canada . |
| 0034298 | 8/1981 | European Pat. Off. . |
| 133004 | 11/1978 | German Democratic Rep. . |
| 10272 | 4/1975 | Japan . |
| 703560 | 12/1979 | U.S.S.R. . |
| 1349050 | 3/1974 | United Kingdom . |

OTHER PUBLICATIONS

J. Fergason, "Liquid Crystals", *Scientific American*, 211, pp. 76–85 (1964).

A. Jarrett et al., "The Effects of Vitamin A on the Skin and its Role as a Cosmetic Agent", *Cosmetics: Research and Technology*, 11th International I.F.S.C.C. Congress, 1, pp. 141–149 (1980).

M. Karasek, "Effect of All-Trans-Retinoic Acid on Human Skin Epithelial Cells in Vitro", *J. Soc. Cosmet. Chem.*, 21, pp. 925–932 (1970).

I. Lubowe, "The Use of Vitamins in Dermatology", *J. Applied Nutrition*, 27, pp. 17–25 (1975).

S. Rubin, "Percutaneous Absorption of Vitamins", *J. Soc. Cosmetic Chem.*, 11, pp. 160–164 (1960).

*Primary Examiner*—H. M. S. Sneed
*Assistant Examiner*—James Saba
*Attorney, Agent, or Firm*—Richard M. Barnes; John J. Cassingham

[57] ABSTRACT

Cosmetic and pharmaceutical compositions and methods comprising delivery systems for the controlled release and enhanced penetration of biologically active materials (e.g., Vitamin A) to the skin. The delivery systems comprise cholesteric liquid crystals wherein the active material is retained within the lamellar molecular structure (i.e., between the molecular sheets) of the cholesteric liquid crystal.

11 Claims, No Drawings

LIQUID CRYSTAL CONTAINING COSMETIC AND PHARMACEUTICAL COMPOSITIONS AND METHODS FOR UTILIZING SUCH COMPOSITIONS

TECHNICAL FIELD OF THE INVENTION

This invention relates to liquid crystal containing compositions and methods for using such compositions. The compositions of the invention are useful for making cosmetics and pharmaceuticals for application to the skin, and particularly for moisturizing and restoring the youthful appearance of the skin. The liquid crystal containing compositions comprise a delivery system for the controlled release and enhanced penetration of biologically active materials such as Vitamin A, and provide an attractive appearance to the cosmetic and pharmaceutical compositions of the invention.

BACKGROUND OF THE INVENTION

Vitamin A is known to possess skin conditioning properties. U.S. Pat. No. 4,603,146 refers to Vitamin A acid (retinoic acid) for retarding the effects of aging of the skin. For a general discussion of dermatological uses of Vitamin A, reference may be had to Thomas et al., *J. Am. Acad. Derm.*, Vol. 4, No. 5 (1981).

Vitamin A is a mild irritant. It is generally applied to the skin in a suitable non-toxic, dermatologically acceptable carrier in an amount and at a frequency which are insufficient to cause excessive irritation of the skin. Most compositions for applying Vitamin A to the skin are in the form of cloudy emulsions or grease-like masses.

Cosmetic and pharmaceutical compositions for applying biologically active materials to the skin typically include a carrier for the active materials in the composition. The selection of a suitable carrier for use in compositions in which the release of biologically active materials is controlled is complicated by the fact that the carrier should not interfere with (and preferably enhances) the ability of the composition to release its active material at a suitable rate. In addition, it is desirable if the carrier (or some other component of the composition) functions to enhance the penetration of the composition's biologically active materials to the desired layers of the skin.

U.S. Pat. No. 4,301,023 (the '023 patent) refers to a mixture of two or more cholesteric liquid crystal compounds, suspended in an oleaginous carrier or in an aqueous emulsion, for moisturizing and softening the skin. The '023 patent does not refer to the use of such liquid crystals as a delivery vehicle for biologically active materials. Neither does the '023 patent disclose that the liquid crystals enhance the penetration of and stabilize active materials contained therein.

SUMMARY OF THE INVENTION

One object of the present invention is to provide compositions and methods useful for restoring the youthful appearance of the skin.

Another object of this invention is to provide compositions useful for cosmetic or pharmaceutical use that comprise an improved delivery system for the controlled release of biologically active materials to the skin.

Yet another object of this invention is to provide improved compositions for enhancing the penetration of biologically active materials into or through skin without damaging the skin or causing adverse systemic effects.

Still another object of this invention is to provide compositions having one or more of the foregoing desireable characteristics and that are visually attractive and pleasant to use.

This invention achieves these and other objects by providing, in one embodiment, a composition comprising a biologically active material (e.g., Vitamin A palmitate) entrapped within the lamellar structure of a cholesteric liquid crystal, the liquid crystal-active material mixture being suspended in a carrier. Preferably, the carrier is a translucent or transparent gel that serves to stabilize the liquid crystals and protect them from degradation.

We have discovered that cholesteric liquid crystals provide an effective delivery vehicle for biologically active materials. The lamellar molecular structure of such cholesteric liquid crystals entraps the active material and controls its release to the skin. The liquid crystals also serve to stabilize certain active materials (e.g., Vitamin A palmitate) that are susceptible to degradation by luminous radiation. In addition, certain active materials (e.g., Vitamin A palmitate) tend to cloud transparent and translucent gels when they are incorporated directly into such gels, but when they are incorporated as part of the liquid crystals useful in the invention they have no such clouding effect. Further, biologically active materials such as Vitamin A palmitate can be intimately combined with the liquid crystals, without destroying the attractive appearance of such crystals.

As used herein, the term "cholesteric liquid crystal" includes any cholesteric liquid that exists in a mesophase. Suitable cholesteric liquid crystals for use in this invention are listed in the '023 patent identified here as well as in U.S. Pat. Nos. 3,998,860, 3,766,061, 3,576,761 and 3,529,156.

As used herein, the term "carrier" shall include any liquid, gel, fluid, ointment, cream, lotion or the like, which is suitable for use in contact with the skin and which does not interact with the other components of the composition in a deleterious manner.

As used herein, the term "biologically active material" includes any material or substance suitable for topical administration to the skin that induces a desired cosmetic or pharmaceutical effect in the skin. For example, the biologically active material may be selected from the group consisting of antibiotics, anti-inflammatory agents, rubefacients, sunscreens, emollients, vitamins and skin protectants. The compositions of the invention may take the form of cosmetic formulations such as hand creams, deodorants, antiperspirants, body powders, lip ices, lip sticks, baby creams and lotions, medicated facial creams and lotions, shampoos, shaving creams, pre- and after-shave lotions and hairgrooming preparations.

The preferred carrier for use in this invention comprises a transparent or translucent polyacrylic gel. We believe that the preferred gels for use in our composition form a polymeric skin around the liquid crystals, which skin serves to protect the liquid crystals. We further believe that this skin also functions to provide a second barrier (the first barrier being the liquid crystal lattice itself) to impede the release of the biologically active materials to the skin, thereby enhancing the controlled release of biologically active materials to the skin.

The compositions of the invention may be applied in effective amounts to the skin in any suitable manner. The amount applied and the frequency of application will, of course, vary depending on the composition being applied to the skin and the effect desired.

DETAILED DESCRIPTION OF THE INVENTION

Either a single cholesteric liquid crystal or a mixture of cholesteric liquid crystals may be used in the compositions of the invention. Depending on the specific liquid crystal or mixture of liquid crystals used, the liquid crystal component of the invention can be widely varied (i.e., cholesteric liquid crystals and mixtures of liquid crystals are known that exhibit yellow, orange, red, green, blue and other colors depending on the temperature of the composition).

Representative cholesteric liquid crystals useful for making the compositions of the invention are cholesteryl nonanoate, cholesteryl benzoate, cholesteryl cinnamate, cholesteryl adipate, cholesteryl p-nitrobenzoate, cholesteryl 2-ethylhexanoate, cholesteryl chloride, cholesteryl oleyl carbonate, cholesteryl cetyl carbonate, cholesteryl ethyl carbonate, cholesteryl methyl carbonate and cholesteryl isostearyl carbonate. A preferred mixture consists of cholesteryl nonanoate, cholesteryl chloride and cholesteryl oleyl carbonate.

The cholesteric materials for making the liquid crystals for use in our invention are typically obtained from the supplier in the form of powders. The materials may be processed into the form of liquid crystals by raising the temperature of the powder to melt the cholesteric material into a mesophase.

Preferably, the biologically active material in the compositions of our invention is present in an amount of from about 1% to 15% by weight of the biologically active material based on the total weight of the cholesteric liquid crystals and biologically active material in the composition. Particularly preferred is about 2% to 10% by weight of the biologically active material.

A particularly preferred biologically active material for use in the compositions and methods of the invention is Vitamin A or a Vitamin A containing material. Particularly preferred is Vitamin A palmitate. Preferably, the Vitamin A palmitate is present in an amount by weight of about 0.1% of the composition.

We prefer to use highly purified Vitamin A palmitate in the compositions of our invention. Such material can be obtained from Roche Chemical Company of Nutley, N.J. The amount of Vitamin A palmitate should be controlled at a level below that at which the Vitamin A palmitate begins to function as a solvent for the liquid crystal, but in a suitable amount to function effectively as a skin conditioner. The total composition preferably contains at least about 1.7 million International Units of Vitamin A.

In use, the Vitamin A functions to make lines and wrinkles in the skin less noticeable. This function is particularly desirable in the area around the eyes.

The amount of the cholesteric liquid crystals that desirably are included in our composition will vary depending on the identity of the liquid crystals. Typically, if the composition contains about 3% by weight or less of the liquid crystals it will be non-tacky and be suitable for application to the skin.

As the percentage of liquid crystals in the composition rises above about 3% by weight, the composition typically begins to exhibit excessive tackiness. This tackiness can be controlled by including an emollient in the liquid crystal solution. Because such emollients tend to reduce the iridescence of the liquid crystals, the use of such high percentages of liquid crystals, with resultant use of emollients, is not preferred.

Carbopol gelling agent containing carriers are the preferred carriers for use in our invention. Such gelling agents, which comprise an acrylic acid polymer, are available commercially from B. F. Goodrich. Carbopol 940 is a particularly preferred gelling agent. Other useful gelling agents that may be used in our composition include Laponite (sodium magnesium silicate), Veegum (aluminum magnesium silicate), Methocel (hydroxypropyl methylcellulose) and Natrosol (hydroxyethylcellulose).

The carrier of this invention may also have incorporated therein a number of carrier additives suitable for cosmetic or pharmaceutical use. For example, other polyacrylic copolymers might be incorporated in the carrier as additional gelling agents. A fragrance may also be included. In addition, polyethelene glycol may be added as a viscosity builder. Similarly, substances such as dyes and pigments may be included to enhance the appearance of the compositions of the invention.

Although not part of the invention, the compositions of the invention include as a carrier additive a collagen-containing mixture. A composition of our invention that contains such a mixture is described in the example below.

Vitamin E and its derivatives may be utilized in admixture with Vitamin A palmitate as an antioxidant to help stabilize the Vitamin A and further enhance the condition of the skin. Other antioxidants may also be incorporated as part of the liquid crystals. Suitable antioxidants include BHT and BHA.

The cholesteric liquid crystal-biologically active material mixture and the carrier of the composition of the invention may be combined using any of various methods for combining two or more phases known to those skilled in the packaging and containerizing art. See, for example, U.S. Pat. Nos. 4,506,710, 4,159,028, and 4,015,644.

The following example is presented for the sole purpose of further illustrating the present invention and is not to be taken as limiting thereto. Unless otherwise specified, all parts and percentages are by weight.

EXAMPLE

This example illustrates the production of a cholesteric liquid crystal, Vitamin A palmitate and carrier gel containing product having the following composition:

| Component | % by weight |
|---|---|
| Cholesteric Liquid Crystal Solution | 2.2504 |
| Vitamin A Palmitate | 0.0696 |
| Carrier Gel with Additives | 97.6800 |

1. Preparation of Cholesteric Liquid Crystal Solution

To prepare a cholesteric liquid crystal solution, we first combine and mix together three cholesteric esters as follows: cholesteryl oleyl carbonate (40.0%), cholesteryl chloride (30.0%) and cholesteryl nonanoate (30.0%). We heat the mixture to about 98° C. and gently stir it by hand until uniform. We then allow the resulting liquid crystal solution to cool to room temperature.

2. Combination of the Cholesteric Liquid Crystal Solution and the Vitamin A Palmitate We combine the cholesteric liquid crystal solution with a composition of Vitamin A palmitate, made by Roche Chemical Company, Nutley, N.J., by gently mixing an amount of Vitamin A palmitate into the cholesteric liquid crystal solution by hand until uniform. The resulting mixture contains 97.0000% cholesteric liquid crystal solution and 3.0000% Vitamin A palmitate, based on the total weight of the resulting mixture.

3. Preparation of Carrier Gel with Additives

We prepare a TEA-acrylamide copolymer gelling agent solution by adding TEA-polyacrylamide copolymer to a mixture of deionized water and Germall so that the resulting solution includes 0.7500% TEA-polyacrylamide copolymer, 0.2000% Germall and 99.0500% deionized water.

We then combine a collagen mixture, which can be obtained, for example, from Chemisches Laboratorium Dr. Kurt Richter GmbH, Berlin, West Germany, with triethanolamine 99% organic base and a 2% aqueous dispersion of Carbopol 940. We combine these components so that the resulting mixture contains 1.0000% triethanolamine 99% organic base, 28.6000% Carbopol 940 dispersion, and 70.4000% collagen mixture.

We then prepare a collagen-containing solution by combining the above collagen-containing mixture with the above TEA-acrylamide copolymer solution to form a solution comprising 36.9100% TEA-acrylamide copolymer solution, based on the total weight of the resulting collagen-containing solution.

We then combine 1,3 butylene glycol plasticizer (2.9304%), glycerine USP 95% thickening agent (2.9304%), acrylic acid polymer (2% dispersion) (24.4200%) and propylene glycol (4.8840%). We add these materials in the amount necessary to obtain a final product having the stated weight percentages of the materials. Unless otherwise stated, the percentage of each material stated hereunder is also stated in terms of the percentage of the material in the final product.

We next add a 3.5% dispersion of Carbopol 940 (14.6520%). Then we prepare a solution of triethanolamine 99% (0.7326%) and deionized water (16.1660%) and add the resulting triethanolamine solution to the mixture. Finally, we combine the collagen-containing solution (30.9646%) with the mixture to obtain a viscous hydrogel carrier having a collagen mixture as a carrier additive.

4. Combination of the Cholesteric Liquid Crystal-Vitamin A Palmitate Mixture and the Carrier Gel with Additives We prepare the cholesteric liquid crystal-Vitamin A palmitate mixture in a pressurized vessel having an outlet tube, the tube ending in a needle. We insert the needle in the carrier gel with additives and apply pressure to force the cholesteric liquid crystal-Vitamin A palmitate mixture through the tube and needle and into the carrier gel. We control the pressure and movement of the needle so as to inject the mixture into the carrier gel. The final product comprises an iridescent blue cholesteric liquid crystal-Vitamin A palmitate mixture (2.3200%) dispersed in a translucent carrier gel (97.6800%).

We claim:

1. A composition comprising vitamin A or a vitamin A containing material, a cholesteric liquid crystal and a translucent or transparent polyacrylic gel carrier, wherein said vitamin A or vitamin A containing material is present in the composition in an amount of about 1% to about 15% by weight of said vitamin A or vitamin A containing material and said cholesteric liquid crystal, and said liquid crystal is present in an amount of about 1% to about 5% by weight of the total composition, said composition providing for the sustained release of the vitamin A or vitamin A containing material into or through the skin of a mammal and for moisturizing and conditioning the skin of said mammal.

2. A method for providing for the sustained release of vitamin A or a vitamin A containing material into or through the skin of a mammal and for moisturizing and conditioning the skin of said mammal comprising applying to said skin an effective amount of the composition of claim 1.

3. The composition of claim 1, wherein the biologically active material is Vitamin A palmitate.

4. The composition of claim 3, wherein the biologically active material further comprises Vitamin E or Vitamin E containing material.

5. The composition of claim 3, wherein the Vitamin A palmitate is present in the composition in an amount of from about 0.1% to about 0.5% by weight of the composition.

6. A method for providing for the sustained release of vitamin A or a vitamin A containing material into or through the skin of a mammal and for moisturizing and conditioning the skin of said mammal comprising applying to said skin an effective amount of the composition of claim 3.

7. A method for providing for the sustained release of vitamin A or a vitamin A containing material into or through the skin of a mammal and for moisturizing and conditioning the skin of said mammal comprising applying to said skin an effective amount of the composition of claim 5.

8. A method for providing for the sustained release of vitamin A or a vitamin A containing material into or through the skin of a mammal and for moisturizing and conditioning the skin of said mammal comprising applying to said skin an effective amount of the composition of claim 6.

9. The composition of claim 1, wherein the liquid crystal is iridescent.

10. The composition of claim 1, wherein the liquid crystal is present in an amount of about 2-3% by weight of the composition.

11. The composition of claim 1, wherein the biologically active material is present in an amount of about 2-10% by weight of the biologically active material and the cholesteric liquid crystal.

* * * * *

UNITED STATES PATENT AND TRADEMARK OFFICE
CERTIFICATE OF CORRECTION

PATENT NO. : 4,999,348
DATED : March 12, 1991
INVENTOR(S) : Cioca et al.

It is certified that error appears in the above-identified patent and that said Letters Patent is hereby corrected as shown below:

Col 6, line 52, Change "6", -- 4 --.

Signed and Sealed this

First Day of March, 1994

Attest:

BRUCE LEHMAN

Attesting Officer  Commissioner of Patents and Trademarks